(12) United States Patent
Kürzinger

(10) Patent No.: US 6,306,453 B1
(45) Date of Patent: *Oct. 23, 2001

(54) ANTI-STRESS AGENTS FOR AQUATIC ANIMALS

(75) Inventor: Hubert Kürzinger, Melle (DE)

(73) Assignee: Warner-Lambert Company, Morris Plains, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/029,388

(22) PCT Filed: Aug. 22, 1996

(86) PCT No.: PCT/EP96/03689

§ 371 Date: Jun. 8, 1998

§ 102(e) Date: Jun. 8, 1998

(87) PCT Pub. No.: WO97/08960

PCT Pub. Date: Mar. 13, 1997

(30) Foreign Application Priority Data

Sep. 5, 1995 (DE) .............................. 195 32 682

(51) Int. Cl.⁷ .................................................. A23G 3/00
(52) U.S. Cl. ........................... 426/658; 424/442; 514/54; 514/55
(58) Field of Search .......................... 426/658; 424/442; 514/54, 55

(56) References Cited

FOREIGN PATENT DOCUMENTS

| | | |
|---|---|---|
| 4335454 | 4/1995 | (DE) . |
| 0466037 | 12/1997 | (EP) . |
| 2674755 | 10/1992 | (FR) . |
| 57012937 | 1/1982 | (JP) . |
| 58175451 | 10/1983 | (JP) . |
| 2250832 | 10/1990 | (JP) . |
| 6048949 | 2/1994 | (JP) . |
| 6271470 | 9/1994 | (JP) . |
| 1271520 | 11/1986 | (RU) . |
| 1788893 | 1/1993 | (RU) . |
| 9504467 | 2/1995 | (WO) . |

OTHER PUBLICATIONS

Siwicki et al. "Dietary Intake of Immunostimulants by Rainbow Trout Affects Non–Specific Immunity & Protection Against Furunculosis", *Vet. Immunol. Immunopath,* vol. 41(2): 125–139, 1994.*

Kanazawa et al. "Nutritional Requirements of Prawn –I. Feeding on Artificial Diet. " *Bull. Japan. Soc. Sci. Fish.*, vol. 36(9): 949–954, 1970.*

Lall et al. "Role of Vitamins and β–Glucans on Immune Response and Disease Resistance in Atlantic Salmon", *Bull. of Aqua. Assoc. Canada*, vol. 95–2: 41–44, Jun. 1995.*

Verlhac et al. Influence of Dietary Glucan and Vitamin C on Non–Specific and Specific Immune Responses of Rainbow Trout (Oncorhynchus my Kiss) *Aquaculture*, vol. 143: 123–133, 1996.*

Leslie Alhadeff, M.D., C. Thomas Gualtieri, M.D. and Morris Lipton, M.D., Ph.D.; "Toxic Effects of Water–Soluble Vitamins, " Nutrition Reviews, vol. 42, No. 2, Feb. 1984, pp. 33–40.

* cited by examiner

*Primary Examiner*—Ralph Gitomer
*Assistant Examiner*—Devesh Khare
(74) *Attorney, Agent, or Firm*—Darryl C. Little; Evan J. Federman

(57) ABSTRACT

The present invention concerns anti-stress agents for improving the resistance of aquatic animals and especially of fish, shrimps and invertebrates in fresh and sea water in the case of strains of all kinds, which can also be used as anti-stress agents for warm and cold water decorative fish, said agents containing a vitamin or a combination of vitamins in megadoses and one or more immune stimulators.

7 Claims, No Drawings

ANTI-STRESS AGENTS FOR AQUATIC ANIMALS

Anti-stress agents for aquatic animals

The present invention is concerned with anti-stress agents for the improvement of the resistance of aquatic animals, especially of fish, shrimps and invertebrates, in fresh and sea water, in the case of stresses of all kinds, which are also usable as anti-stress agent for warm and cold water decorative fish, said agents containing a vitamin or a combination of vitamins in megadoses and one or more immune stimulators.

The use is known from AU 92 10 574 of immune stimulators, for example glucan, for protection against bacterial and viral infectious diseases in shrimps. Administration takes place via the feed in a dosing of 0.001–10%. As in JP 22 18 615, in EP-A-0 466 037 is described the increasing of the resistance of fish and shrimps toward pathogens. The dry feed contains 5–100 mg glucan per kg of feed. In EP-A-0 384 323 is described the synergistic effect of a vaccination against Aeromonas in the case of fish by simultaneous administration of 15–20 mg glucan via the feed per kg of body weight. Furthermore, from EP-A-0 559 450 is known the use of glucan as a binding agent in fish feed.

The vitamin contents in the natural raw materials usually employed which are worked up to mixed feeds for aquatic animals are mostly not sufficient in order to prevent deficiency symptoms. To the most frequent nutritionally caused diseases belong vitamin deficiency phenomena. For this reason, vitamins are usually added to feedstuffs for fish and shrimps in amounts covering the requirements.

Commercially usual dosagings are described, for example in NRC, Nutrient Requirements of Warmwater Fishes and Shellfishes, 1983. The recommended commercially usual value requirements for vitamins for fish, for example Cyprinus carpio L., amount, per kg of feed, to 10000 IU of vitamin A, 500 to 1000 IU of vitamin D, 30 mg of Vitamin E, 1 mg of vitamin $B_1$, 9 mg of vitamin $B_2$, 3 mg of vitamin $B_6$, 60 mg of vitamin C, 10 to 20 mg of pantothenic acid and 14 mg of nicotinic acid. Statements of need for vitamin $B_{12}$, vitamin K, inositol, choline, folic acid and vitamin C equivalent from long-stable vitamin C phosphate are not documented.

The effects of overdosages of vitamins by the use of megadoses of vitamins have been described in the scientific literature (see, for example, Steffens: Grundlagen der Fischernährung, 1985). In the case of the investigations, it was primarily observed whether hypervitaminoses, such as increased mortality, reduced growth, unfavourable feed utilisation, strong defects caused by overdosages of vitamins, occurred, for example by the feeding of $3.75 \times 10^6$ IU of vitamin $D_3$/kg of feed; $2 \times 10^6$ IU of vitamin A/kg of feed; 5 g of vitamin E/kg of feed; 10 g of nicotinic acid/kg of feed. However, the examined megadoses showed no negative effects.

Surprisingly, we have now found that anti-stress agents, especially feed materials or aqueous suspensions for the introduction into the living water, containing an overdosage of one or more vitamins in combination with one or more immune stimulators, are outstandingly suitable for increasing the resistance of aqueous animals in the case of strains of all kinds but especially due to stress.

Stress situations occur almost permanently in the case of aquatic animals and lead to a strong straining of the animals. Examples of stress situations are hunger, high occupation density, water change, changes of the water parameters, territorial battles, aggressive behaviour, handling, medicinal therapy, transport and diseases.

Therefore, the subject of the present invention are anti-stress agents for aquatic animals, especially fish, shrimps and invertebrates, in fresh and sea water, containing at least one vitamin or a vitamin combinating in an overdosing (megadose) and at least one immune stimulator. Preferred immune stimulators include poly-saccharides, for example glucan, zymosan, mannan, lichenan, postulan, lentinan, schizophyllan, scleroglucan, M-glucan, yeast glucan, muramyl dipeptide and chitin. Further iminune stimulators which can be used according to the present invention include lactoferrin, lactoperoxidases, glycyrrhizins, diaminopimelic acid peptide derivatives, for example N-[(R)-6-carboxy-N2-[N-(1-oxoheptyl)-D-gamma-glutamyl]-L-lysyl)-D-alanine, levamisole, inosiplex, 4-methyluracil, tilorone, dipyridamole and azimexone. Furthermore, plant and bacterial extracts can also be used, for example extracts of Phytolacca, Bryoria, Baptisia, aloes, Aristolochia, Arnica, mistletoe, Echinacea, palmetto, *Eleutherococcus senticosus, Rosa roxburghii, Artemisiae argyi folium, Brassica oleracea* var. *capitata*, sterilized *Clostridium butyricum miyairi* and *Saccharomyces cerevisiae*.

The immune stimulator is present in the anti-stress agent in an amount of from 0.0001 to 10% by weight and preferably of 0.1% by weight. The preferred immune stimulator is β-glucan.

The vitamins are used in an overdosing of 2.5 fold up to 5000 fold of the recommended requirement values. The water- and/or fat-soluble vitamins are preferably dosed in the following ranges (per kg of feedstuff):

| | |
|---|---|
| vitamin A | $3 \times 10^4$–$2 \times 10^6$ IU |
| vitamin D | $1.5 \times 10^3$–$1 \times 10^6$ IU |
| vitamin E | 90 mg–10 g |
| vitamin $B_1$ | 3 mg–5 g |
| vitamin $B_2$ | 27 mg–10 g |
| vitamin $B_6$ | 9 mg–5 g |
| vitamin $B_{12}$ | 0.1 μg–5 mg |
| Vitamin C | 180 mg–50 g |
| Vitamin K | 20 mg–5 g |
| pantothenic acid | 30 mg–5 g |
| nicotinic acid | 42 mg–50 g |
| inositol | 1 g–50 g |
| choline | 200 mg–50 g |
| folic acid | 0.1 mg–5 g |
| vitamin C equivalent | 0.1 mg–5 g |

| | |
|---|---|
| vitamin A | $2.8 \times 10^5$ IU |
| vitamin D | $2.5 \times 10^3$ IU |
| vitamin E | 1.9 g |
| vitamin $B_1$ | 330 mg |
| vitamin $B_2$ | 950 rng |
| vitamin $B_6$ | 190 mg |
| vitamin $B_{12}$ | 820 μg |
| vitamin C | 6.35 g |
| vitamin K | 96 mg |
| pantothenic acid | 940 mg |
| nicotinic acid | 4.7 g |
| inositol | 7.3 g |
| choline | 1.13 g |
| folic acid | 96 mg |
| vitamin C equivalent | 4.9 |
| β-glucan | 1 g |

If chitin is to be used as immune stimulator, then this is preferably prepared according to JP 6271470. For example, 10 g of chitin PSH are mixed with 150 ml 36% hydrochloric acid and stirred at ambient temperature for 2 hours. The reaction is ended by the addition of 1 l of distilled water and the product is filtered off and washed with distilled water.

The novel anti-stress agent for aquatic animals was tested via the feed on territorial, territory-forming decorative fish (*Cichlasoma nicaraguense*) regarding stress behaviour in comparison with the control (without meladoses of vitamins and without immune stimulators), in each case with three parallels. Besides the permanently present social stress, in addition, in each aquarium stress was induced daily by stirring the pond several times with a fish collecting net.

The high losses of 19% in the control group are to be attributed to the increased stress due to the aggressive behaviour and, above all, to the increased stress due to the treatment with the collecting net. Animals of all sizes were thereby affected. Perch fed with the experimental feed showed, on the basis of the feed which contained megadoses of vitamins and an immune stimulator, almost no deaths (1% mortality).

The anti-stress agent according to the present invention can be administered via the feed as flocks, extrudates, pellets and tablets in a dry, moist or semi-moist state or in liquid form into the water. The use can take place prophylactically or also in the case of acute strains of the aquatic animals.

The administration of the anti-stress agent takes place in a combination of megadoses of one or more vitamins and one or more immune stimulators.

What is claimed is:

1. An anti-stress feed for aquatic animals, comprising:
a.) from $3\times10^4$ to $2\times10^6$ IU per kg of feed of vitamin A; and
b.) at least one immunostimulating agent selected from the group consisting of glucan, zymosan, mannan, lichenan, pustulan, lentinan, schizophyllan, scleroglucan, M-glucan, yeast glucan, muramyl dipeptide, chitin, lactoferrin, lactoperoxidases, glycyrrhizin, immunostimulating peptides containing diaminopimelic acid, N-[(R)-6-carboxy-N2-[N-(-1-oxoheptyl)-D-γ-glutamyl]-L-lysyl]-D-alanine, levamisole, inosiplex, 4-methyluracil, tilorone, dipyridamole, azimexone, extracts of Phytolacca, extracts of Bryoria, extracts of Baptisia, aloes, extracts of Aristolochia, extracts of Arnica, mistletoe, extracts of Echinacea, palmetto, extracts of *Eleutherococcus senticosus, Rosa roxburghii, Artemixtiae argyi folium, Brassica oleracea* var. *capitata*, sterilized *Clostridium butyricum miyairi*, and *Saccharomyces cerevisiae*.

2. An anti-stress feed for aquatic animals, comprising:
a.) from $3\times10^4$ to $2\times10^6$ IU per kg of feed of vitamin A; and
b.) at least one immunostimulating agent selected from the group consisting of extracts of Phytolacca, extracts of Bryoria, extracts of Baptisia, aloes, extracts of Aristolochia, extracts of Arnica, mistletoe, extracts of Echinacea, palmetto, extracts of *Eleutherococcus senticosus, Rosa roxburghii, Artemixtiae argyi folium, Brassica oleracea* var. *capitata*, sterilized *Clostridium butyricum miyairi*, and *Saccharomyces cerevisiae*.

3. An anti-stress feed for aquatic animals, comprising:
a.) at least one immunostimulating agent selected from the group consisting of glucan, zymosan, mannan, lichenan, pustulan, lentinan, schizophyllan, scleroglucan, M-glucan, yeast glucan, muramyl dipeptide, lactoferrin, lactoperoxidases, glycyrrhizin, immunostimulating peptides containing diaminopimelic acid, N-[(R)-6-carboxy-N2-[N-(-1-oxoheptyl)-D-γ-glutamyl]-L-lysyl]-D-alanine, levamisole, inosiplex, 4-methyluracil, tilorone, dipyridamole, azimexone, extracts of Phytolacca, extracts of Bryoria, extracts of Baptisia, aloes, extracts of Aristolochia, extracts of Arnica, mistletoe, extracts of Echinacea, palmetto, extracts of *Eleutherococcus senticosus, Rosa roxburghii, Artemixtiae argyi folium, Brassica oleracea* var. *capitata*, sterilized *Clostridium butyricum miyairi*, and *Saccharomyces cerevisiae*; and
b.) per kg of feed a megadosage of a vitamin selected from the group consisting of $3\times10^4$ to $2\times10^6$ IU vitamin A, 20 mg to 5 gm vitamin K, and mixtures thereof.

4. An anti-stress feed for aquatic animals, comprising:
a.) at least one immunostimulating agent selected from the group consisting of extracts of Phytolacca, extracts of Bryoria, extracts of Baptisia, aloes, extracts of Aristolochia, extracts of Arnica, mistletoe, extracts of Echinacea, palmetto, extracts of *Eleutherococcus senticosus, Rosa roxburghii, Artemixtiae argyi folium, Brassica oleracea* var. *capitata*, sterilized *Clostridium butyricum miyairi*, and *Saccharomyces cerevisiae*; and
b.) per kg of feed a megadosage of a vitamin selected from the group consisting of $3\times10^4$ to $2\times10^6$ IU vitamin A, 20 mg to 5 gm vitamin K, and mixtures thereof.

5. An anti-stress feed for aquatic animals, comprising:
a.) at least one immunostimulating agent selected from the group consisting of glucan, zymosan, mannan, lichenan, pustulan, lentinan, schizophyllan, scleroglucan, M-glucan, yeast glucan, muramyl dipeptide, chitin, lactoferrin, lactoperoxidases, glycyrrhizin, immunostimulating peptides containing diaminopimelic acid, N-[(R)-6-carboxy-N2-[N-(-1-oxoheptyl)-D-γ-glutamyl]-L-lysyl]-D-alanine, levamisole, inosiplex, 4-methyluracil, tilorone, dipyridamole, azimexone, extracts of Phytolacca, extracts of Bryoria, extracts of Baptisia, aloes, extracts of Aristolochia, extracts of Arnica, mistletoe, extracts of Echinacea, palmetto, extracts of *Eleutherococcus senticosus, Rosa roxburghii, Artemixtiae argyi folium, Brassica oleracea* var. *capitata*, sterilized *Clostridium butyricum miyairi*, and *Saccharomyces cerevisiae*; and
b.) per kg of feed a megadosage of a vitamin selected from the group consisting of $2.8\times10^5$ IU vitamin A, 1.9 vitamin E, 330 mg vitamin $B_1$, 950 mg vitamin $B_2$, 190 vitamin $B_6$, 820 µg vitamin $B_{12}$, 6.35 g vitamin C, 96 mg vitamin K, 940 mg pantothenic acid, 4.7 g nicotinic acid, 7.3 g inositol, 1.13 g choline, 96 mg folic acid, 4.9 g vitamin C equivalent and mixtures thereof.

6. An anti-stress feed for aquatic animals, comprising:
a.) at least one immunostimulating agent selected from the group consisting of extracts of Phytolacca, extracts of Bryoria, extracts of Baptisia, aloes, extracts of Aristolochia, extracts of Arnica, mistletoe, extracts of Echinacea, palmetto, extracts of *Eleutherococcus senticosus, Rosa roxburghii, Artemixtiae argyi folium, Brassica oleracea* var. *capitata*, sterilized *Clostridium butyricum miyairi*, and *Saccharomyces cerevisiae*; and
b.) per kg of feed a megadosage of a vitamin selected from the group consisting of $2.8\times10^5$ IU vitamin A, 1.9 g vitamin E, 330 mg vitamin $B_1$, 950 mg vitamin $B_2$, 190 vitamin $B_6$, 820 µg vitamin $B_{12}$, 6.35 g vitamin C, 96 mg vitamin K, 940 mg pantothenic acid, 4.7 g nicotinic acid, 7.3 g inositol, 1.13 g choline, 96 mg folic acid, 4.9 g vitamin C equivalent and mixtures thereof.

7. An anti-stress feed according the claim 5 wherein the immunostimulating agent is present at a concentration of 1 g per kg of feed and wherein the immunostimulating agent is β-glucan.

* * * * *